(12) United States Patent
Wang et al.

(10) Patent No.: US 11,219,655 B2
(45) Date of Patent: Jan. 11, 2022

(54) ABORTION MEDICATIONS AND ADMINISTRATION METHOD THEREOF

(71) Applicant: YUNNAN KANG-ZHOU BIOTECH CO., LTD., Yunnan (CN)

(72) Inventors: Kangmin Wang, Yunnan (CN); Hong Zhao, Yunnan (CN); Guizhen Lu, Yunnan (CN); Chun Wu, Yunnan (CN); Lifen Zhang, Yunnan (CN); Chenghuan Yang, Yunnan (CN); Jingjing Wang, Yunnan (CN)

(73) Assignee: YUNNAN KANG-ZHOU BIOTECH CO., LTD., Kunming (CN)

( * ) Notice: Subject to any disclaimer, the term of this patent is extended or adjusted under 35 U.S.C. 154(b) by 4 days.

(21) Appl. No.: 16/720,108

(22) Filed: Dec. 19, 2019

(65) Prior Publication Data
US 2020/0121751 A1   Apr. 23, 2020

Related U.S. Application Data

(63) Continuation of application No. PCT/CN2018/090733, filed on Jun. 12, 2018.

(51) Int. Cl.
*A61K 36/48* (2006.01)
*A61K 9/00* (2006.01)
*A61K 47/26* (2006.01)
*A61K 47/42* (2017.01)

(52) U.S. Cl.
CPC .......... *A61K 36/48* (2013.01); *A61K 9/0034* (2013.01); *A61K 47/26* (2013.01); *A61K 47/42* (2013.01)

(58) Field of Classification Search
None
See application file for complete search history.

(56) References Cited

U.S. PATENT DOCUMENTS 6,110,891 A * 8/2000 Pusztai ............... A61K 38/18
424/85.1

FOREIGN PATENT DOCUMENTS

| CN | 102274486 A | 12/2011 |
| CN | 103157095 A | 6/2013 |
| CN | 103920140 A | 7/2014 |
| CN | 107213453 A | 9/2017 |
| JP | 2004231555 | * 1/2003 |
| JP | 2004231555 | * 8/2004 ............. A61K 38/00 |

OTHER PUBLICATIONS

Yang Chenghuan et al., Placenta cellular and tissue changes after administration of phytohemagglutinin from red kidney bean for termination of middle-late pregnancy in mice[J]. Chinese Journal of Family Planning, 2015, 23 (8): 524-529.
Zhang Lifen, et al., Effect of phytohemagglutinin (PHA) from Yunan white kidney bean on development of mouse embryos [J]. China Journal of Chinese Materia Medica, 2011 (12): 1665-1669.
Zhang Lifen, et al., Effect of administration phytohemagglutinin from Yunan white kidney bean on termination of middle and late pregnancy in mice, Abstracts from the 23rd National Congress of the Chinese Physiological Society and the Academic Conference of the Physiological Society, Oct. 18, 2010, p. 336.

* cited by examiner

Primary Examiner — Melissa S Mercier

(57) ABSTRACT

The invention relates to medicines, and more particularly to an abortion medication and an administration thereof, where the abortion medication contains 40-60 mg/mL of a kidney bean lectin. The invention also provides another abortion medication, which contains 40-60 mg/mL of a kidney bean lectin, 40-50 mg/mL of an oligosaccharide and 6-9 mg/mL of NaCl. The two abortion medications provided herein are both capable of effectively terminating the pregnancy and are safe without toxic side effects. Moreover, these drugs can be reused several times. These abortion medications are administered intrauterinely, which enables the kidney bean lectin therein to show the best abortive effect, and the local administration of these drugs in the uterine cavity has relatively simple operation.

18 Claims, No Drawings

ABORTION MEDICATIONS AND ADMINISTRATION METHOD THEREOF

CROSS-REFERENCE TO RELATED APPLICATIONS

This application is a continuation of International Patent Application No. PCT/CN2018/090733, filed on Jun. 12, 2018, which claims the benefit of priority from Chinese Patent Application No. 201710473112.2, filed on Jun. 21, 2017. The contents of the aforementioned applications, including any intervening amendments thereto, are incorporated herein by reference.

TECHNICAL FIELD

This application relates to medicines, and more particularly to an abortion medication and an administration method thereof.

BACKGROUND OF THE INVENTION

Currently, unwanted pregnancy occurs more and more frequently, and there are two primary methods for terminating the pregnancy, including surgical abortion and medical abortion.

In the process of surgical abortion, the reproductive tract will be inevitably damaged due to the operation in uterine cavity, and it will be painful so that those who are physically weak may suffer from shock. In addition, if the equipments used in the surgery are not clean enough or otherwise, the reproductive organ will be prone to infection. By contrast, medical abortion is often preferred by those who are afraid of surgery, since it is free of the use of artificial appliances, thereby avoiding genital injuries or infections. At present, the commonly-used abortion medication is mifepristone, which should be used within 72 h after the unprotected sex, while for the established termination of pregnancy, mifepristone is recommended to be used within 49 days after the pregnancy.

However, in the practical application, the existing drugs for terminating unwanted pregnancy can only work within a certain period of time, for example, during the period of 72 h to 35 d after the unprotected sex, since the corpus luteum has not been completely developed and fails to provide targets for mifepristone, the pregnancy will not be terminated after the use of mifepristone. Currently, there is still lack of methods for effectively terminating the pregnancy during the period of 72 h to 35 d after the unprotected sex. Moreover, the existing drugs are all administered orally (i.e., systemic administration), so that they will affect the neuroendocrine center and peripheral endocrine glands after the absorption. Most of the available abortion medications reveal obvious side effects, such as nausea, emesis, vertigo, fatigue, headache, breast tenderness and lower abdominal pain.

SUMMARY OF THE INVENTION

An object of this application is to provide an abortion medication to overcome the defects in the prior art.

Technical solutions of this application are described as follows.

This application provides an abortion medication, comprising 40-60 mg/mL of a kidney bean lectin.

In an embodiment, the abortion medication further comprises an oligosaccharide, NaCl and a buffer solution.

In an embodiment, the oligosaccharide has a concentration of 20-50 mg/mL, preferably 40-50 mg/mL.

In an embodiment, the oligosaccharide is selected from the group consisting of isomaltooligosaccharide, fructooligosaccharide, stachyose, raffinose and a combination thereof, preferably stachyose, raffinose or a combination thereof.

In an embodiment, NaCl has a concentration of 6-9 mg/mL, preferably 7-9 mg/mL, and more preferably 7-8 mg/mL.

In an embodiment, the buffer solution is a $Na_2HPO_4$—$NaH_2PO_4$ buffer or a $K_2HPO_4$—$KH_2PO_4$ buffer.

In an embodiment, the kidney bean lectin is a red kidney bean lectin, a white kidney bean lectin or a combination thereof.

In an embodiment, the abortion medication further comprises a thickening agent, where the thickening agent has a concentration of 4-20 mg/mL, preferably 6-17 mg/mL, and more preferably 10-15 mg/mL.

In an embodiment, the thickening agent is selected from the group consisting of *Bletilla striata* gelatin, *Tremella fuciformis* polysaccharide, sodium carboxymethyl cellulose and a combination thereof, preferably selected from the group consisting of *Tremella fuciformis* polysaccharide, sodium carboxymethyl cellulose and a combination thereof, and more preferably *Tremella fuciformis* polysaccharide.

In an embodiment, the abortion medication further comprises an anaesthetic, where the anaesthetic has a concentration of 0.2-0.8 mg/mL, preferably 0.4-0.6 mg/mL, and more preferably 0.5-0.6 mg/mL.

In an embodiment, the anaesthetic is lidocaine, or optionally a composition of lidocaine and PEG 10000.

In an embodiment, the abortion medication further comprises a pharmaceutically-acceptable carrier; wherein the carrier is selected from the group consisting of water, alcohol, an antiseptic and a combination thereof.

In an embodiment, the kidney bean lectin has an agglutinating activity equal to or larger than 1/128 mg/mL.

In an embodiment, the abortion medication can be prepared into a gel, a paste or a solution. This application further provides another abortion medication, comprising 40-60 mg/mL of a kidney bean lectin, 40-50 mg/mL of an oligosaccharide, 6-9 mg/mL of NaCl and a buffer solution.

This application further provides an administration method of the abortion medication, comprising:

administering the abortion medication in a uterine cavity by injection, preferably administering the abortion medication topically in the uterine cavity.

In an embodiment, the "administering the abortion medication in a uterine cavity by injection" specifically comprises:

1-9 days after an unprotected or accidental intercourse, sterilizing a vulva in a supine position; dilating a vagina with a vaginal speculum to expose a cervical orifice; inserting a delivery tube through the cervical orifice into the uterine cavity to administer the abortion medication; or 10-60 days after the unprotected or accidental intercourse, sterilizing the vulva in a supine position or genucubital position; dilating the vagina with the vaginal speculum to expose the cervical orifice; inserting the delivery tube through the cervical orifice into the uterine cavity to administer the abortion medication.

In an embodiment, in the case of 1-9 days after the unprotected or accidental intercourse, the abortion medication is administered at a dosage of 3-4 mL; and in the case of 10-60 days after the unprotected or accidental intercourse, the abortion medication is administered at a dosage of 4-6 mL.

The abortion medication provided herein has the following beneficial effects.

It has been found in the research that the Yunnan Kidney bean lectin (KBL) (or phytohemagglutinin (PHA)) has galactose, mannose and acetylglucosamine binding sites, where the galactose is closely related to the embryo implantation. Specifically, there are a large number of galactosyl groups on the surfaces of the embryo and the endometrium, and if the galactosyl groups are blocked, the implantation of the embryo will be significantly inhibited. Therefore, the kidney bean PHA can be used to terminate the embryo implantation through the binding to the galactosyl group, where especially in the case of a concentration of 40-60 mg/mL in the abortion medication, the kidney bean PHA can effectively terminate the 10 to 60-day pregnancy and shows no toxic side effects on human. In this stage of pregnancy, the kidney bean PHA is capable of: (1) acting on the endometrium, glandular epithelium and basement membrane to interfere with the implantation of embryo; (2) acting on embryonic trophoblast and basement membrane; (3) acting on decidual cells and the surrounding extracellular matrix; and (4) specifically acting on the syncytiotrophoblast of a placenta during the postimplantation stage. In addition, since the kidney bean PHA is a non-immunogenic substance, it will not lead to the antigen-antibody reaction, immunological memory and toxic side effects after use. The oligosaccharide, NaCl and buffer solution employed herein can optimize the effect of the abortion medication, allowing for a better therapeutic effect.

DETAILED DESCRIPTION OF EMBODIMENTS

The invention will be clearly and completely described below with reference to the embodiments to render the objects, technical solutions and advantages of the invention clearer. The conditions in the embodiments which are not specified are performed in a conventional manner or a manner recommended by the manufacturer. The reagents or instruments of which the manufacturers are not specified are all commercially-available.

An abortion medication in an embodiment of the invention is specifically described as follows.

In an embodiment, the invention provides an abortion medication, including a kidney bean lectin, where the kidney bean lectin has a concentration of 40-60 mg/mL, such as 40 mg/mL, 45 mg/mL, 50 mg/mL, 55 mg/mL and 60 mg/mL.

In an embodiment, the invention also provides another abortion medication, including 40-60 mg/mL of a kidney bean lectin, 40-50 mg/mL of an oligosaccharide, 6-9 mg/mL of NaCl and a buffer solution.

The fertilized egg undergoes early embryonic development immediately after the fertilization at the oviduct, and then enters the uterus from the oviduct about 6-9 days after the fertilization. At this time, the endometrium thickens and the number of sugar groups increases. A recognition occurs between the embryo and the endometrium, and then the embryo is implanted into the endometrium through the three processes of positioning, adhesion and penetration. During the implantation, the sugar group plays a vital role in the implantation since the recognition between the embryo and the endometrium is determined by the sugar group on the surface of the embryo. If there is a problem occurring to the sugar group on the embryo or endometrium, the embryo will fail to be successfully implanted. There are a large number of galactosyl groups on the surfaces of the embryo and the endometrium, so that if the galactosyl groups are blocked, the implantation of the embryo will be significantly interfered. Considering that the kidney bean PHA has a galactose binding site, it is suitable as a drug to terminate the embryo implantation. Moreover, the kidney bean PHA is a non-immunogenic substance, so that it will not result in antigen-antibody reaction and immunological memory, rendering it suitable as a healthy and safe component in the abortion medication. The kidney bean PHA can be reused several times.

In an embodiment, the kidney bean lectin can be a red kidney bean lectin or a white kidney bean lectin, and is not specifically limited herein.

It has been observed that the effect of the kidney bean lectin on the target cell varies with its concentration. Specifically, the kidney bean lectin can induce the cell apoptosis at a moderate concentration, and cause the cell necrosis at a high concentration. Therefore, in the spatial dimension, the kidney bean lectin can act on the embryo and the surrounding environment thereof; in the time dimension, the kidney bean lectin is capable of specifically binding to the embryo, endometrium and trophoblastic cells to exert the effect in the stages of non-pregnancy, pre-implantation and post-implantation, which is the basis of the unique function of the kidney bean lectin to terminate pregnancy, that is, the effect of the kidney bean lectin is exerted by direct contact and reaction.

In an embodiment, the abortion medication can be prepared into a gel, a paste or a solution. In an embodiment, the abortion medication is intrauterinely administered, and specifically, the abortion medication is intrauterinely administered by injection. Through the intrauterine injection, the kidney bean lectin can be directly bound to the glandular epithelium and basement membrane of the endometrium, embryonic trophoblast and its basement membrane, decidual cells and surrounding extracellular matrix and the syncytiotrophoblast of the placenta, optimizing the abortion effect. Additionally, the intrauterine topical administration also involves simple operation.

Since the kidney bean lectin is a glycoprotein with a molecular weight of about 32 kD, it will not affect the level of endocrine hormones in advanced parts of the neuroendocrine axis such as hypothalamus and pituitary after locally administered in the uterine cavity.

In an embodiment, based on the intrauterine administration, a concentration of the oligosaccharide in the abortion medication can be 20-50 mg/mL, such as 20 mg/mL, 23 mg/mL, 25 mg/mL, 28 mg/mL, 30 mg/mL, 35 mg/mL, 37 mg/mL, 40 mg/mL, 45 mg/mL and 50 mg/mL. In addition, the kidney bean lectin plays a role in increasing the number of *Lactobacillus* in the vagina, and the oligosaccharide is able to effectively promote the growth of beneficial bacteria in the vagina to reduce the occurrence of vaginal infection during the administration. The oligosaccharide also has a certain protective effect on proteins, and can promote the cell growth at an appropriate concentration. Therefore, the introduction of oligosaccharide in the formula is absolutely beneficial to human body.

In an embodiment, the oligosaccharide is isomaltooligosaccharide, fructooligosaccharide, stachyose or raffinose. Since stachyose or raffinose is naturally present in a lectin extract, the external addition is not required herein. In an embodiment, the oligosaccharide is at least one of stachyose and raffinose, such as stachyose, raffinose or a combination thereof.

In an embodiment, in order to prevent the drug from flowing out of the vagina during the intrauterine administration, the abortion medication is further introduced with a thickening agent to be prepared into a gel. Further, in order to ensure the fluidity of the abortion medication and improve the specific binding to the embryo, endometrium and trophoblast cell, a concentration of the thickening agent may be 4-20 mg/mL, such as 4 mg/mL, 6 mg/mL, 10 mg/mL, 12 mg/mL, 15 mg/mL, 17 mg/mL and 20 mg/mL.

There are a wide variety of thickening agents, such as *Bletilla striata* gelatin, which are not specifically exemplified herein. In an embodiment, the thickening agent is at least one of *Tremella fuciformis* polysaccharide and sodium carboxymethyl cellulose, such as *Tremella fuciformis* polysaccharide, sodium carboxymethyl cellulose or a combination thereof, where the *Tremella fuciformis* polysaccharide, as a basidiomycete immunopotentiator, can also improve the body's immune function and boost the level of leukocytes.

In an embodiment, in order to prevent the pregnant woman from suffering from pain during the administration, the abortion medication can be further introduced with an anaesthetic. However, since a high concentration of the anaesthetic may easily cause side effects and a low concentration of the anaesthetic will fail to provide desired effect, the anaesthetic preferably has a concentration of 0.2-0.8 mg/mL in the abortion medication, such as 0.2 mg/mL, 0.4 mg/mL, 0.5 mg/mL, 0.6 mg/mL and 0.8 mg/mL, which can ensure a desired anesthetic effect.

In an embodiment, the anesthetic is lidocaine, preferably a composition of lidocaine and PEG 10000.

In an embodiment, in order to ensure the normal physiological activities of the cells in the uterus during the administration, a concentration of NaCl in the abortion medication is controlled to 6-9 mg/mL, such as 6 mg/mL, 7 mg/mL, 7.5 mg/mL, 8 mg/mL and 9 mg/mL, to ensure the normal osmotic pressure of cells.

In an embodiment, the buffer solution is a $Na_2HPO_4$—$NaH_2PO_4$ buffer or a $K_2HPO_4$—$KH_2PO_4$ buffer, which is used to regulate the intrauterine pH, avoiding the infection caused by changes in the intrauterine environment. The buffer solution can be prepared according to the actual requirements. Herein, a pH 5.8 $Na_2HPO_4$—$NaH_2PO_4$ buffer is exemplarily prepared, (1) 31.2 g of $NaH_2PO_4.2H_2O$ (or 27.6 g of $NaH_2PO_4.H_2O$) was dissolved in 1000 mL of redistilled water to produce a 0.2 mol/L $NaH_2PO_4$ solution; (2) 71.632 g of $Na_2HPO_4.12H_2O$ (or 53.6 g of $Na_2HPO_4.7H_2O$ or 35.6 g of $Na_2HPO_4.2H_2O$) is dissolved in 1000 mL of redistilled water to produce a 0.2 mol/L $Na_2HPO_4$ solution; and (3) 92 mL of the 0.2 mol/L $NaH_2PO_4$ solution is mixed with 8.0 mL of the 0.2 mol/L $Na_2HPO_4$ solution to produce the required buffer.

In an embodiment, the abortion medication of the invention further includes a pharmaceutically-acceptable carrier, such as water, alcohol and an antiseptic, where the antiseptic can effectively extend the shelf life of the abortion medication.

In an embodiment, the administration of the abortion medication can be accordingly adjusted according to the time to obtain a better effect.

Specifically, 1-9 days after an unprotected or accidental intercourse, the vulva of a pregnant woman is sterilized in a supine position, and the vagina is dilated with a vaginal speculum to expose a cervical orifice. Then a delivery tube is inserted through the cervical orifice into the uterine cavity to administer the abortion medication, where the delivery tube may be a disposable plastic rectal delivery tube having a length of 9 cm and an outer diameter of 0.2 cm. In an embodiment, the abortion medication provided herein is preferably administered at a dosage of 3-4 mL 1-9 days after the unprotected or accidental intercourse.

10-60 days after an unprotected or accidental intercourse, the vulva of a pregnant woman is simply sterilized in a supine position or genucubital position, and the vagina is dilated with a vaginal speculum to expose a cervical orifice. Then a delivery tube is inserted through the cervical orifice into the uterine cavity to administer the abortion medication, where the delivery tube may be a disposable plastic rectal delivery tube having a length of 9 cm and an outer diameter of 0.2 cm. In an embodiment, the abortion medication provided herein is preferably administered at a dosage of 4-6 mL 1-9 days after the unprotected or accidental intercourse. In an embodiment, the invention further provides a method of preparing the abortion medication, including mixing a kidney bean lectin with other components, where a concentration of the kidney bean lectin in the abortion medication is 40-60 mg/mL.

It should be specified that in some embodiments, the extraction, purification and activity determination of the kidney bean lectin are performed according to Chinese Patent Publication No. 101508730A, and the protein content is determined using a conventional biuret method. It should be noted that in some embodiments, the kidney bean lectin is required to have an aggregation activity equal to or larger than 1/128 mg/mL.

The features and properties of the invention will be further described below with reference to the examples.

Example 1

In this example, the invention provided an abortion medication, including a kidney bean lectin, an oligosaccharide, NaCl and a buffer solution, where the kidney bean lectin had a concentration of 45 mg/mL, the oligosaccharide was stachyose and had a concentration of 30 mg/mL, NaCl had a concentration of 8 mg/mL, and the buffer solution was a pH 5.8 $Na_2HPO_4$—$NaH_2PO_4$ buffer.

Example 2

In this example, the invention provided an abortion medication, including a kidney bean lectin, an oligosaccharide, NaCl and a buffer solution, where the kidney bean lectin had a concentration of 40 mg/mL, the oligosaccharide was raffinose and had a concentration of 45 mg/mL, NaCl had a concentration of 9 mg/mL, and the buffer solution was a pH 5.8 $Na_2HPO_4$—$NaH_2PO_4$ buffer.

Example 3

In this example, the invention provided an abortion medication, including a kidney bean lectin, an oligosaccharide, NaCl and a buffer solution, where the kidney bean lectin had a concentration of 40 mg/mL, the oligosaccharide was isomaltooligosaccharide and had a concentration of 45 mg/mL, NaCl had a concentration of 9 mg/mL, and the buffer solution was a pH 5.8 $Na_2HPO_4$—$NaH_2PO_4$ buffer.

Example 4

In this example, the invention provided an abortion medication, including a kidney bean lectin, an oligosaccharide, NaCl, an anaesthetic and a buffer solution, where the kidney bean lectin had a concentration of 60 mg/mL, the oligosaccharide was fructooligosaccharide and had a concentration of 28 mg/mL, NaCl had a concentration of 8 mg/mL, the buffer solution was a pH 5.8 Na$_2$HPO$_4$—NaH$_2$PO$_4$ buffer, and the anaesthetic was a composition of lidocaine and PEG 10000 and had a concentration of 0.7 mg/mL.

Example 5

In this example, the invention provided an abortion medication, including a kidney bean lectin, an oligosaccharide, NaCl, a thickening agent and a buffer solution, where the kidney bean lectin had a concentration of 45 mg/mL, the oligosaccharide was stachyose and had a concentration of 35 mg/mL, NaCl had a concentration of 8 mg/mL, the buffer solution was a pH 5.8 Na$_2$HPO$_4$—NaH$_2$PO$_4$ buffer, and the thickening agent was sodium carboxymethyl cellulose and had a concentration of 15 mg/mL.

Example 6

In this example, the invention provided an abortion medication, including a kidney bean lectin, an oligosaccharide, NaCl, a thickening agent and a buffer solution, where the kidney bean lectin had a concentration of 45 mg/mL, the oligosaccharide was stachyose and had a concentration of 35 mg/mL, NaCl had a concentration of 8 mg/mL, the buffer solution was a pH 5.8 Na$_2$HPO$_4$—NaH$_2$PO$_4$ buffer, and the thickening agent was *Tremella fuciformis* polysaccharide and had a concentration of 15 mg/mL.

Example 7

In this example, the invention provided an abortion medication, including a kidney bean lectin, an oligosaccharide, NaCl, a thickening agent, an anaesthetic and a buffer solution, where the kidney bean lectin had a concentration of 40 mg/mL, the oligosaccharide was stachyose and had a concentration of 30 mg/mL, NaCl had a concentration of 7 mg/mL, the buffer solution was a pH 5.8 Na$_2$HPO$_4$—NaH$_2$PO$_4$ buffer, the thickening agent was sodium carboxymethyl cellulose and had a concentration of 10 mg/mL, and the anaesthetic was a composition of lidocaine and PEG 10000 and had a concentration of 0.3 mg/mL.

Experimental Example

1. Animal Experiment
(1) Acute Toxicity Test of Kidney Bean PHA

80 Kunming mice (40 males and 40 females), weighing 18-22 g, were collected, and respectively measured for the LD$_{50}$ of red kidney bean PHA after intraperitoneal injection. The 40 female mice and 40 male mice were averagely divided into 5 groups according to the dosage of the red kidney bean PHA, respectively. Respective mice received a single intraperitoneal injection of 0.4 mL red kidney bean PHA, and were subsequently observed for 7 d. It can be concluded from the results that the tolerance of the mouse to PHA varied in sex, specifically, the female mice had a LD$_{50}$ of 725.07 mg/kg, of which a 95% confidence interval was 639.65-827.14 mg/kg, a LD$_0$ of 440 mg/kg and a LD$_{100}$ of 1074 mg/kg; while the male mice had a LD$_{50}$ of 535.45 mg/kg, of which a 95% confidence interval was 480.96-598.81 mg/kg, a LD$_0$ of 350 mg/kg and a LD$_{100}$ of 783.64 mg/kg. No abnormalities were found in the dead mice after necropsy, and no significant abnormalities were observed in the weight, diet, appearance, behavior, secretions and excreta of the surviving mice.

(2) Influence of Kidney Bean PHA on Mice after Intrauterine Administration

Investigated herein was the effect of high concentration of kidney bean PHA on mice. 48 non-pregnant female mice were prepared, and randomly and averagely divided into 6 groups, and the 6 groups were respectively denoted as 50 mg-group, 20 mg-group, 10 mg-group, 5 mg-group and normal saline group. As the name suggests, respective mice in the 50 mg-group underwent unilateral intrauterine injection of 50 mg kidney bean PHA; accordingly, respective mice in the 20 mg-group, 10 mg-group and 5 mg-group respectively underwent unilateral intrauterine injection of 20 mg, 10 mg and 5 mg of kidney bean PHA; and respective mice in the normal saline group underwent unilateral intrauterine injection of 0.5 mL of normal saline. Then the mice of each group were observed for the death, and the results were shown in Table 1.

TABLE 1

Mortality of mice intrauterinely injected with different concentrations of kidney bean PHA

| | Kidney Bean PHA (mg) | | | | Normal |
|---|---|---|---|---|---|
| | 50 | 20 | 10 | 5 | Saline |
| Mortality (%) | 37.5 | 12.5 | 0 | 0 | 0 |

It can be seen from Table 1 that no death was observed in the mice from the 5 mg-group, 10 mg-group and the normal saline group after the unilateral intrauterine injection, while the unilateral intrauterine injection of 20 mg and 50 mg of kidney bean PHA respectively resulted in a mortality of 12.5% and 37.5%. Therefore, a unilateral uterine injection of 10 mg kidney bean PHA or less will not cause death in mice.

(3) Influence of Concentration of Kidney Bean PHA on Embryonic Development of Mice Female mice, aged 6-10 weeks, were subcutaneously injected with 7.5-10 IU of pregnant mare serum gonadotropin (PMSG), and then intraperitoneally injected with the same dose of human chorionic gonadotropin (HCG) 48 h later. After that, the female mice were allowed to cohabit with male mice, and examined for the vaginal plug in the next morning, where the day when the vaginal plug occurred was defined as the 1$^{st}$ d. On the 2$^{nd}$ d, 2-cell embryos were collected and averagely divided into 10 groups. Then the embryos were respectively transferred to medium droplets, and then cultured at 37° C. and 5% CO$_2$ under saturated humidity in a CO$_2$ incubator for 72-96 h, where the embryos were observed every 24 h. The development of embryos in each group was recorded 96 h later. The experiment was repeated 5 times, and the results were shown in Table 2.

TABLE 2

Influence of concentration of kidney bean PHA on mouse 2-cell embryos cultured in vitro (72 h)

| Content of PHA in M16 (µg/ml) | Number of 2-cell embryos (n) | Number of trials (n) | Stage (%) | | | | |
|---|---|---|---|---|---|---|---|
| | | | 4-8 cell | Morula | Blastocyst | Hatched Blastocyst | Fragmentation rate |
| Control 0 | 85 | 8 | 73 (85.9)$^a$ | 67 (78.8)$^a$ | 61 (71.8)$^b$ | 9 (14.7)$^b$ | 4 (4.7)$^a$ |
| Purified product 50 | 86 | 8 | 81 (94.2)$^a$ | 78 (90.7)$^a$ | 74 (86.0)$^a$ | 29 (39.2)$^a$ | 3 (3.5)$^a$ |
| Purified product 100 | 86 | 8 | 77 (89.5)$^a$ | 73 (84.9)$^a$ | 70 (81.4)$^a$ | 22 (31.4)$^a$ | 3 (3.5)$^a$ |
| Crude extract 50 | 87 | 8 | 75 (86.2)$^a$ | 70 (80.5)$^a$ | 66 (75.6)$^b$ | 17 (25.8)$^b$ | 5 (5.7)$^a$ |
| Crude extract 100 | 87 | 8 | 77 (88.5)$^a$ | 74 (85.0)$^a$ | 67 (77.0)$^b$ | 20 (29.9)$^a$ | 5 (5.7)$^a$ |
| Crude extract 200 | 87 | 8 | 79 (90.8)$^a$ | 77 (88.5)$^a$ | 74 (85.1)$^a$ | 25 (34.7)$^a$ | 6 (6.9)$^a$ |
| Crude extract 500 | 86 | 7 | 71 (82.6)$^a$ | 65 (75.6)$^a$ | 59 (68.6)$^b$ | 10 (16.9)$^b$ | 6 (7.0)$^a$ |
| Crude extract 1000 | 82 | 7 | 27 (32.9)$^c$ | 8 (9.8)$^c$ | 0 (0)$^c$ | 0 (0)$^c$ | 0 (0)$^c$ |
| Crude extract 2000 | 88 | 7 | 5 (5.7)$^c$ | 0 (0)$^c$ | 0 (0)$^c$ | 0 (0)$^c$ | 0 (0)$^c$ |
| Crude extract 5000 | 89 | 7 | 0 (0)$^c$ | 0 (0)$^c$ | 0 (0)$^c$ | 0 (0)$^c$ | 0 (0)$^c$ |

Notes:
the comparison is made between respective experimental groups and control group, where a:b, $P < 0.05$; a:c, $P < 0.01$; and hatched blastocyst (%) = the number of hatched blastocyst/the number of blastocysts.

It can be seen from Table 2 that the embryos of the purified product 50-group had the highest blastocyst formation rate (86.0%), and the blastocyst formation rates of the purified product 50-group, the purified product 100-group and the crude extract 200-group were both significantly higher than that of the control ($P<0.05$). No significant difference was observed between the crude extract 100-group and the control. In addition, the hatched blastocyst formation rates of the purified product 50-group, the purified product 100-group, the crude extract 100-group and the crude extract 200-group were all significantly higher than the control ($P<0.05$). With respect to the crude extract 1000-group, there were only an extremely small number of embryos developing into the morulas, and most of the embryos were stagnated at the 2-cell and 4-cell stages. In the crude extract 2000-group and the crude extract 5000-group, the embryos were almost completely stagnated or degenerated at the 2-cell stage. In the medium containing 5000 µg/mL of kidney bean PHA crude extract, the embryos suffered from cell membrane rupture and died. The 2-cell embryos cultured in the medium containing 1000 µg/mL of kidney bean PHA crude extract were stagnated at the 2-cell stage, and suffered from cytoplasm expansion and vacuolation.

(4) Influence of Repeated Use of Kidney Bean PHA on Subsequent Embryonic Development of Mouse Female Kunming mice were treated by superovulation and then cohabited with male mice, where the mice in which the vaginal plug was observed were regarded as the experimental group. On the 14$^{th}$ day after the occurrence of vaginal plug, 0.05 mL (5 mg) of the kidney bean PHA was injected from the unilateral uterine horn to terminate the pregnancy. The mice suffering from abortion were allowed to have a rest for 10 d, and aborted again in the same way. Then the mice undergoing two miscarriages were allowed to have a rest for 10 d again and cohabited with male mice to conceive again, and their offspring was observed. There were a total of 7 female mice in this experimental group successfully undergoing two consecutive conception-abortion processes and re-conception. At the same time, 7 untreated female mice of the same age as the experimental group were used as a control group, cohabited to conceive and allowed to produce offspring. The offspring was consecutively observed for 8 weeks (i.e., the offspring was sexually mature) and recorded for some indexes, including the number of offspring, sex ratio, weight change, change in body length and tail length, auricle separation time, incisor eruption time and eye opening time. The results indicated that compared to the control group, the repeated abortion did not affect the re-pregnancy of the mice in the experimental group, but the offspring was slightly smaller in the average number, and slightly faster in the growth rate. No significant difference was observed in other indexes.

(5) Effect on Termination of Early and Midtrimester Pregnancy in Mice

Female mice, aged 6-10 weeks, were subcutaneously injected with 7.5-10 IU of PMSG, and then injected intraperitoneally with hCG of the same dose 48 h later. After that, the mice were cohabited with male mice, and examined for the vaginal plug in the next morning, where the day when the vaginal plug occurred was defined as the 1$^{st}$ day of pregnancy, and the day following the occurrence of the vaginal plug was defined as the 2$^{nd}$ day of pregnancy, and so on. 80 randomly-prepared pregnant female mice were averagely divided into 8 groups, including: (1) 1$^{st}$ d-pregnancy group; (2) 3$^{rd}$ d-pregnancy group; (3) 5$^{th}$ d-pregnancy group; (4) 7$^{th}$ d-pregnancy group; (5) 8$^{th}$ d-pregnancy group; (6) 9$^{th}$ d-pregnancy group; (7) 10$^{th}$ d-pregnancy group and (8) 11$^{th}$ d-pregnancy group, where groups (1) and (2) were in a pre-implantation stage; group (3) was in an implantation stage; groups (4), (5) and (6) were in early pregnancy; and groups (7) and (8) were in midtrimester pregnancy. The mice were anaesthetized, fixed in a prone position and opened with a longitudinal mouth at the midline of the skin slightly to the rear part of the back. Then the mice were cut at the muscles of the back on the uterus on both sides. The uterus at one side was pulled out and ligated at a position closest to the bifurcation of the cervix, where the ligation was only performed on the uterine corpus and the blood vessels should be avoided. After the uterus at the other side was pulled out, an injection was slowly made at the uterine horn (at an end near the fallopian tube). 5 mice in respective groups were treated with the kidney bean PHA, specifically, the uterus at one side was ligated and the uterus at the other side was injected with 0.1 mL (10 mg) of PHA. The other 5 mice in respective groups, as the control group, were ligated at the uterus at one side and injected with 0.1 mL of normal saline at the uterus at the other side.

The mice in respective groups all underwent cesarean section on the 20$^{th}$ d of the pregnancy to observe the uterine morphology, and the numbers of normal fetuses and stillborn fetuses were respectively recorded.

The experimental results were statistically processed by chi-square test and variance analysis, and the results of the experimental group were shown in Table 3.

TABLE 3

Influence of unilateral uterine injection of kidney bean PHA on mouse embryonic development in different stages of pregnancy

| Stage of pregnancy (day) | Litter size and rate (%) of the uterus at the ligation side | Litter size and rate (%) of the uterus injected with normal saline | Litter size and rate (%) of the uterus injected with kidney bean PHA |
| --- | --- | --- | --- |
| Day 1  | 3 (10)$^b$ | 0 (0)$^a$ | 0 (0)$^a$ |
| Day 3  | 0 (0)$^a$  | 0 (0)$^a$ | 0 (0)$^a$ |
| Day 5  | 0 (0)$^a$  | 0 (0)$^a$ | 0 (0)$^a$ |
| Day 7  | 2 (10)$^b$ | 7 (20)$^b$ | 0 (0)$^a$ |
| Day 8  | 2 (10)$^b$ | 3 (20)$^b$ | 0 (0)$^a$ |
| Day 9  | 2 (20)$^b$ | 3 (40)$^c$ | 0 (0)$^a$ |
| Day 10 | 3 (20)$^b$ | 5 (40)$^c$ | 0 (0)$^a$ |
| Day 11 | 0 (0)$^a$  | 7 (60)$^c$ | 0 (0)$^a$ |

Notes:
in the same column, $^{a;b}$, $P < 0.05$; $^{b;c}$, $P < 0.05$; and $^{a;c}$, $P < 0.01$.

It can be seen from Table 3 that from the 1$^{st}$ d from the 11$^{th}$ d of the pregnancy, the uterus injected with the kidney bean PHA had a litter size and rate both of 0. The variance analysis demonstrated that there were significant differences in the litter rates among mice in the ligation group, the kidney bean PHA group and the normal saline group. The pregnancy and littering were observed in both of the ligation group and the normal saline group. The results confirmed that in different gestational stages of mice (1$^{st}$ d-11$^{th}$ d), the pregnancy can be completely terminated by intrauterine injection of kidney bean PHA, and the uteruses injected with normal saline had a litter rate increasing with the extension of the gestation period.

(2) Clinical Trial

Clinical subject: XX, Zhao, female, 24 years old, without parturition experience.

The last menstrual period was Feb. 17, 2015. After the occurrence of nausea and vomiting of pregnancy, the clinical subject received the first B-ultrasonography for the lower abdomen in Shengai Chinese Medicine Hospital in Kunming on April 3. The results indicated that the posterior uterus had a size of 8.4*6.2*5.1 cm, and a gestational sac having a size of 1.4*1.0 was present in the uterus. Further, a yolk sac and embryo bud tissues were observed in the gestational sac, where the embryo bud had a length of about 0.6 cm, in which original heart heat was observed. No obvious abnormal echo was found in the bilateral adnexas.

It can be speculated from the above results that the pregnancy had lasted for 55-60 d. On the morning of Apr. 8, 2015, the clinical subject received a conventional sterilization for the vulva and vagina, and then lay in a supine position. Her vagina was dilated with a vaginal speculum, and a cervix clamp was used to fix the sides of the cervical orifice. Subsequently, a disposable plastic rectal delivery tube having a length of 9 cm and an outer diameter of 0.2 cm was inserted through the cervix into the uterine cavity, and 4 mL of normal saline containing RKBL (a total dose of 20 mg) was slowly injected, where the administration time was 9:40. The delivery tube was immediately removed after the injection, and the clinical subject was allowed to have a rest in bed. 43 min after the injection, the clinical subject suffered from the bearing-down pain at the lower abdomen, and took one ibuprofen sustained release capsule. The abdominal pain disappeared at 12:30, but there was still a fall bilge feeling. At this time, the clinical subject had a blood pressure of 95/70 mmHg and a normal body temperature. At 9:50 am on Apr. 10, 2015, 3 misoprostol tablets (60 mg) were vaginally administered to the subject. At 12:45, the gestational sac was discharged with a bleed volume of about 10 mL, where the gestational sac had a size of 4.5*4.0*1.2 cm, in which a small fetus was observed. At 23:00, dicynone and oxytocin were intramuscularly injected at a dose same as above, and then the clinical subject was checked to have normal blood pressure and body temperature. It was observed that the clinical subject consecutively suffered from bleeding for 8 d from April 10$^{th}$ when there was a bleeding sign to April 17$^{th}$, and the total bleeding volume was 130-145 mL. The next menstruation was postponed to 40 days later, and then returned to normal.

In summary, the invention provides an abortion medication herein, which is capable of termination the 1-60 d pregnancy, thereby solving the problem that there is currently lack of a method for effectively terminating the pregnancy throughout the early unintended pregnancy, especially for the period of 4-35 d after the pregnancy. Moreover, compared to the prior art, the invention can significantly shorten the recovery time and causes smaller damages to women. The invention will not result in the generation of corresponding antibodies, so that it can be repeatedly used. Finally, it will not affect the reproductive endocrine center, and has a relatively simple topical administration.

Described are merely preferred embodiments of the invention, which are not intended to limit the invention. Various modifications, variations and replacements made by those skilled in the art without departing from the spirit of the invention should fall within the scope of the invention.

INDUSTRIAL APPLICABILITY

The abortion medication provided herein has a simple composition, which is beneficial to the processing and industrial production. In addition, it also involves convenient administration and desired abortion effect. Therefore, the invention has a good application prospect in the medical field and suitable for the industrial production.

What is claimed is:

1. An abortion medication comprising a kidney bean lectin, an oligosaccharide, NaCl and a buffer solution;
    wherein a concentration of the kidney bean lectin is 40-60 mg/mL.

2. The abortion medication of claim 1, wherein the oligosaccharide has a concentration of 20-50 mg/mL.

3. The abortion medication of claim 2, wherein the oligosaccharide has a concentration of 40-50 mg/mL.

4. The abortion medication of claim 1, wherein the oligosaccharide is selected from the group consisting of isomaltooligosaccharide, fructooligosaccharide, stachyose, raffinose and a combination thereof.

5. The abortion medication of claim 1, wherein NaCl has a concentration of 6-9 mg/mL.

6. The abortion medication of claim 1, wherein the buffer solution is a $Na_2HPO_4$—$NaH_2PO_4$ buffer or a $K_2HPO_4$—$KH_2PO_4$ buffer.

7. The abortion medication of claim 1, wherein the kidney bean lectin is a red kidney bean lectin, a white kidney bean lectin or a combination thereof.

8. The abortion medication of claim 1, further comprising a thickening agent;
wherein the thickening agent has a concentration of 4-20 mg/mL.

9. The abortion medication of claim 8, wherein the thickening agent is selected from the group consisting of *Bletilla striata* gelatin, *Tremella fuciformis* polysaccharide, sodium carboxymethyl cellulose and a combination thereof.

10. The abortion medication of claim 9, wherein the thickening agent is *Tremella fuciformis* polysaccharide.

11. The abortion medication of claim 9, further comprising an anaesthetic;
wherein the anaesthetic has a concentration of 0.2-0.8 mg/mL.

12. The abortion medication of claim 11, wherein the anaesthetic is lidocaine or a composition of lidocaine and PEG 10000.

13. The abortion medication of claim 12, further comprising a pharmaceutically-acceptable carrier.

14. The abortion medication of claim 13, wherein the carrier is selected from the group consisting of water, alcohol, an antiseptic and a combination thereof.

15. The abortion medication of claim 14, wherein the kidney bean lectin has an agglutinating activity equal to or larger than 1/128 mg/mL.

16. A method for administration of the abortion medication of claim 1, comprising:
injecting the abortion medication in a uterine cavity.

17. The method of claim 16, wherein "injecting the abortion medication in the uterine cavity" comprises:
a) 1-9 days after an unprotected or accidental intercourse, sterilizing a vulva in a supine position; dilating a vagina with a vaginal speculum to expose a cervical orifice; and inserting a delivery tube through the cervical orifice into the uterine cavity to administer the abortion medication; or
b) 10-60 days after an unprotected or accidental intercourse, sterilizing a vulva in a supine position or genucubital position; dilating a vagina with a vaginal speculum to expose a cervical orifice; and inserting a delivery tube through the cervical orifice into the uterine cavity to administer the abortion medication.

18. The administration method of claim 17, wherein in the case of a), the abortion medication is administered at a dosage of 3-4 mL; and in the case of b), the abortion medication is administered at a dosage of 4-6 mL.

* * * * *